United States Patent [19]
Gyuris et al.

[11] Patent Number: 5,672,508
[45] Date of Patent: Sep. 30, 1997

[54] INHIBITORS OF CELL-CYCLE PROGRESSION, AND USES RELATED THERETO

[75] Inventors: Jeno Gyuris, Winchester; Lou Lamphere, Boston, both of Mass.; David Beach, Huntington Bay, N.Y.

[73] Assignee: Mitotix, Inc., Cambridge, Mass.

[21] Appl. No.: 589,981

[22] Filed: Jan. 23, 1996

[51] Int. Cl.$^6$ .............................. C12N 15/62; C07H 21/04
[52] U.S. Cl. ...................... 435/320.1; 536/23.4; 536/23.5
[58] Field of Search ................... 424/93.1, 204.1, 424/450; 435/5, 6, 69.1, 235.1, 240.1, 254.2, 320.1, 240.4; 514/44; 536/23.4, 23.5

[56] References Cited

FOREIGN PATENT DOCUMENTS

| | | |
|---|---|---|
| WO 94/09135 | 4/1994 | WIPO . |
| WO 95/25429 | 9/1995 | WIPO . |
| WO 95/28483 | 10/1995 | WIPO . |

OTHER PUBLICATIONS

Elledge, S. J. et al. (1994) "Cdk inhibitors: on the threshold of checkpoints and development" Curr Opin Cell Biol, vol. 6, pp. 847–852.

Guan K–L et al. (1994) "Growth suppression by p18, a p16$^{INK4/MTS1}$ and p14$^{INK4B/MTS2}$ related cdk6 inhibitor correlates with wild–type pRb function" Genes & Dev. vol. 8, pp. 2939–2952.

Hannon G. and Beach D. (1994) "p15$^{INK4B}$ is a potential effector of TGF–β–induced cell cycle arrest" Nature, vol. 371, pp. 257–261.

Harper J. et al. (1994) "The p21 cdk–interacting protein cip1 is a potenmt inhibitor of G1 cyclin–dependent kinases" Cell, vol. 75, pp. 805–816.

Hiral H. et al. (1995) "novel INK4 proteins, p19 and p18, are specific inhibitors of the cyclin D–dependent kinases cdk4 and cdk6" Moll Cell Biol, vol. 15, No. 5, pp. 2672–2681.

Kamb A. et al (1994) "A cell cycle regulatory potentially involved in genesis of many tumor types" Science, vol. 264, pp. 436–440.

Lee M–H. et al. (1995) "Cloning of p57$^{KIP2}$, a cyclin–dependent kinase inhibitor with unique domain structure and tissue distribution" Genes & Dev. vol. 9; pp. 639–649.

Marx J. (1994) "New tumor suppressor may rival p53" Science vol. 264, pp. 344–345.

Matsuoka S. et al. (1995) "p57$^{KIP2}$, a structurally distinct member of the p21$^{CIP1}$ cdk inhibitor family, is a candidate tumor suppressor gene" Genes & Dev vol. 9; pp. 650–662.

Ming Chan, F.K. et al. (1995) "Identification of human and mouse p19, a novel cdk4 and cdk6 inhibitor with homology to p16$^{INK4}$" Mol Cell Biol, vol. 15, No. 5; pp. 2682–2688.

Ogawa N. et al. (1995) "Functional domains of Pho81p, an inhibitor of Pho85p protein kinase, in the transduction pathway of Pi signals in Saccharomyces cerevisiae" Mol Cell Biol, vol.15, No. 2; pp. 997–1004.

Polyak K. et al. (1994) "p27$^{Kip\,1}$, a cyclin–cdk inhibitor, links transforming growth factor β and contact inhibition to cell cycle arrest." Genes & Dev. vol. 8; pp. 9–22.

Serrano M et al. (1993) "A new regulatory motif in cell–cycle control causing specific inhibition of cyclin D/cdk4" Nature, vol. 366, pp. 704–707.

Xiong Y. et al. (1993) "Subunit rearrangement of the cyclin–dependent kinases is associated with cellular transformation" Genes & Dev. vol. 7, pp. 1572–1583.

Xiong, Y. et al. (1993) "p21 is a universal inhibitor of cyclin kinases" Nature, vol. 366, p. 701–704.

Zhu et. al. p107 uses a p21CIP1–related domain to biind cyclin/cdk2 adn regulate interactions with E2F. Genes and Devel. vol. 9:1740–1752. Sep. 1995.

Primary Examiner—David Guzo
Assistant Examiner—William Sandals
Attorney, Agent, or Firm—Matthew P. Vincent; Beth E. Arnold; Foley, Hoag & Eliot LLP

[57] ABSTRACT

The present invention pertains to novel inhibitors of cyclin-dependent kinases (CDKs), particularly CDK/cyclin complexes, which inhibitors can be used to control proliferation and/or differentiation of cells in which the inhibitors are introduced. More specifically, the inhibitors of the invention are chimeric proteins which include CDK-binding motifs from two or more different proteins. For example, the subject chimeric proteins can be generated from the in-frame fusion of coding sequences from two different CDK inhibitor proteins, such as may be derived from fusion of coding sequences for an INK4 protein and coding sequences for a CIP protein. Chimeric proteins of the present invention have been observed to be more potent inhibitors of cyclin/CDK complexes than were either of the portions of the chimeric protein individually.

37 Claims, No Drawings

INHIBITORS OF CELL-CYCLE PROGRESSION, AND USES RELATED THERETO

BACKGROUND OF THE INVENTION

The cell division cycle is one of the most fundamental processes in biology which, in multicellular organisms, ensures the controlled generation of cells with specialized functions. Under normal growth conditions, cell proliferation is tightly regulated in response to diverse intra- and extracellular signals. This is achieved by a complex network of proto-oncogenes and tumor-suppressor genes that are components of various signal transduction pathways. Activation of a proto-oncogene(s) and/or a loss of a minor suppressor gene(s) can lead to the unregulated activity of the cell cycle machinery. This, in ram, will lead to unregulated cell proliferation and to the accumulation of genetic errors which ultimately will result in the development of cancer (Pardee, Science 246:603–608, 1989).

In the eukaryotic cell cycle a key role is played by the cyclin-dependent kinases (CDKs). Cdk complexes are formed via the association of a regulatory cyclin subunit and a catalytic kinase subunit. In mammalian cells, the combination of the kinase subunits (such as cdc2, CDK2, CDK4 or CDK6) with a variety of cyclin subunits (such as cyclin A, B1, B2, D1, D2, D3 or E) results in the assembly of functionally distinct kinase complexes. The coordinated activation of these complexes drives the cells through the cell cycle and ensures the fidelity of the process (Draetta, Trends Biochem. Sci. 15:378–382, 1990; Sherr, Cell 73:1059–1065, 1993). Each step in the cell cycle is regulated by a distinct and specific cyclin-dependent kinase. For example, complexes of Cdk4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the cdc2/cyclin B complex controls the entry into M-phase (Sherr, Cell 73:1059–1065, 1993).

The CDK complex activity is regulated by mechanisms such as stimulatory or inhibitory phosphorylations as well as the synthesis and degradation of the kinase and cyclin subunit themselves. Recently, a link has been established between the regulation of the activity of cyclin-dependent kinases and cancer by the discovery of a group of CDK inhibitors including the $p27^{KIP1}$, $p21^{Waf1/Cip1}$ and $p16^{Ink4/MTS1}$ proteins. The activity of $P21^{Waf1/Cip1}$ is regulated transcriptionally by DNA damage through the induction of p53, senescence and quiescence (Harper et al., Cell 75:805–816, 1993). The inhibitory activity of $p27^{Kip1}$ is induced by the negative growth factor TGF-β and by contact inhibition (Polyak et al., Cell 78:66–69, 1994). These proteins, when bound to CDK complexes, inhibit their kinase activity, thereby inhibiting progression through the cell cycle. Although their precise mechanism of action is unknown, it is thought that binding of these inhibitors to the CDK/cyclin complex prevents its activation. Alternatively, these inhibitors may interfere with the interaction of the enzyme with its substrates or its cofactors.

While $p21^{Waf1/Cip1}$ and $p27^{Kip1}$ inhibit all the CDK/cyclin complexes tested $P16^{Ink4/MTS1}$, p15, p18 and p19 block exclusively the activity of the CDK4/cyclin D and CDK6/cyclin D complexes in the early G1 phase (Serrano et al., Nature 366:704–707, 1993), by either preventing the interaction of Cdk4 and Cyclin D1, or indirectly preventing catalysis. As mentioned above, the $p21^{Waf1/Cip1}$ is positively regulated by the tumor suppressor p53 which is mutated in approx. 50% of all human cancers. $p21^{Waf1/Cip1}$ may mediate the tumor suppressor activity of p53 at the level of cyclin-dependent kinase activity. $p16^{Ink4/MTS1}$ is the product of a tumor suppressor gene localized to the 9p21 locus, which is frequently mutated in human cancer cells.

Of all the various kinases, the CDK4/cyclin D complexes are known to play an important role in regulating cell cycle progression in early G1. These complexes function as integrators of various growth factor-induced extracellular signals and as a link between the different signal transduction pathways and other cyclin-dependent kinases. The expression of the cyclin D1 positive regulatory subunit, is deregulated by gene translocations, retroviral insertions and amplifications in parathyroid adenomas, lymphomas, esophageal and breast carcinomas. The targeted overexpression of cyclin D1 in the mammary epithelium of transgenic mice induces mammary adenomas and adenocarcinomas. This confirms that cyclin D1, when overexpressed, acta as an oncogene (Wang et al., Nature 369:669–671, 1994). These data supports the idea that the lack of functional $p16^{Ink4/MTS1}$ or the overexpression of cyclin D1 leads to the deregulation of CDK4/cyclin D1 kinase activity and thereby contribute to uncontrolled cell proliferation.

The prominent role of CDK/cyclin kinase complexes, in particular, CDK4/cyclin D kinase complexes, in the induction of cell proliferation and their deregulation in tumors, makes them ideal targets for developing highly specific anti-proliferative agents.

SUMMARY OF THE INVENTION

In one aspect, the present invention relates to a nucleic acid comprising a nucleotide sequence encoding a chimeric polypeptide having at least two CDK-binding motifs derived from different proteins which bind to cyclin dependent kinases (CDKs). The chimeric polypeptide binds to CDKs and inhibits cell-cycle progression.

The chimeric polypeptide can be a fusion protein, or can be generated by chemically cross-linking the CDK-binding motifs.

In preferred embodiments, at least one of the CDK-binding motifs is a CDK-binding motif of a CDK inhibitor protein, such as an INK4 protein, e.g., p15, p16, p18 and p19, or a CIP protein, e.g., $p21^{CIP1}$, $p27^{KIP1}$, and $p57^{KIP2}$. However, it will be understood that other CDK-binding motifs may be useful. Indeed, the CDK-binding motif of the INK4 proteins is characteristized by tandemly arranged ankyrin-like sequences, which sequences exist in other proteins and, for those which are able to bind a CDK, can be used to generate the subject chimeric proteins. Likewise, the CDK-binding motif can be a p21/p27 inhibitory domain of a protein which has some homology with the CIP protein family. An exemplary chimeric protein of the present invention is designated by SEQ ID No. 2, and encoded by the CDS designated in SEQ ID No. 1.

In preferred embodiments, the CDK-binding motifs of the chimeric protein have different binding specificities, relative to one and other, for cyclin dependent kinases. For instance, the chimeric protein can be generated with a CDK-binding motif from a protein which binds to and inhibits a CDK involved in progression of the cell cycle in $G_0$ and/or $G_1$ phase, and another CDK-binding motif from a protein which binds to and inhibits a CDK involved in progression of the cell cycle in S, $G_2$ and/or M phase. That is, the chimeric protein will bind to and inhibit a plurality (two or more) of cyclin dependent kinases which are active in different phases of the cell-cycle.

In most embodiments, the nucleic acid will further include a transcriptional regulatory sequence for controlling transcription of the nucleotide sequence encoding the chimeric polypeptide, e.g., the transcriptional regulatory sequence is operably linked to a chimeric gene encoding the chimeric polypeptide. For example, the present invention specifically contemplates recombinant transfection systems which include: (i) a gene construct including a nucleic acid encoding a chimeric polypeptide comprising CDK-binding motifs from two or more different proteins which bind to cyclin dependent kinases, and operably linked to a transcriptional regulatory sequence for causing expression of the chimeric polypeptide in eukaryotic cells, and (ii) a gene delivery composition for delivering the gene construct to a cell and causing the cell to be transfected with the gene construct. For example, the gene construct can be derived from a viral vector, such as an adenoviral vector, an adeno-associated viral vector or a retroviral vector. In such embodiments, the gene delivery composition comprises a recombinant viral particle. In other embodiments, the gene construct can be delivered by such means as a liposome or a poly-cationic nucleic acid binding agent. For in vivo delivery to a mammal, such as a human, the gene delivery composition will further include a pharmaceutically acceptable carrier for adminstration to an animal, and, as necessary, will be a sterile preparation and substantially free of pyrogenic agents.

The present invention also pertains to preparations of such chimeric polypeptides. e.g., polypeptides which are generated from CDK-binding motifs from two or more different proteins which bind to cyclin dependent kinases. In preferred embodiments, the chimeric polypeptide is formulated in pharmaceutically acceptable carrier for delivery to a mammal. For example, the chimeric polypeptide can be formulated in liposomal preparations.

Still another aspect of the present invention related to transgenic animals which have cells harboring a nucleic acid one of the subject fusion proteins.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbai, A Practical Guide To Molecular Cloning (1984); the treatise, Methods In Enzymology (Academic Press, Inc., N.Y.); Gene Transfer Vectors For Mammalian Cells (J. H. Miller and M. P. Caios eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

DETAILED DESCRIPTION OF THE INVENTION

Progression of eukaryotic cells through the cell cycle is governed by the sequential formation, activation, and subsequent inactivation of a series of cyclin/cyclin dependent kinase complexes. The mechanisms underlying the expression of cyclins and the activation of the different cyclin-CDK complexes needed for progression through successive cell cycle transitions are now fairly well understood. In addition to positive regulation by the activation of cyclin-CDK complexes, negative regulation of the cell cycle occurs at checkpoints, many of which operate to control formation of cyclin/CDK complexes and/or activation of the complexes. Accordingly, these transitions are negatively regulated by signals that constrain the cell-cycle until specific conditions are fulfilled. Entry in to mitosis, for example, is inhibited by incompletely replicated DNA or DNA damage. These restriction on cell-cycle progression are essential for preserving the fidelity of the genetic information during cell division. The transition from $G_1$ to S phase, on the other hand, coordinates cell proliferation with environmental cues, after which the checks on the cell-cycle progression tend to be cell autonomous. Disruption of these signaling pathways can uncouple cellular responses from environmental controls and may lead to unrestrained cell proliferation or abherrent loss of differentiation.

The present invention pertains to novel inhibitors of cyclin-dependent kinases (CDKs), particularly CDK/cyclin complexes, which inhibitors can be used to control proliferation and/or differentiation of cells in which the inhibitors are introduced. More specifically, the inhibitors of the invention are chimeric proteins which include CDK-binding motifs from two or more different proteins. For example, as set forth in greater detail below, the subject chimeric proteins can be generated from the in-frame fusion of coding sequences from two different CDK inhibitor proteins (generically refered to herein as "CKI" proteins), such as may be derived from fusion of coding sequences for an INK4 protein and coding sequences for a CIP protein. Moreover, as the appended examples describe, chimeric proteins of the present invention have been observed to be more potent inhibitors of cyclin/CDK complexes than were either of the portions of the chimeric protein individually. For instance, p27-p16 chimeric proteins inhibited a cyclin D1/CDK4 complex with an $IC_{50}$ more than two-fold less than p27 alone, and ten-fold less than p16 alone. Likewise, the p27-p16 chimeric protein inhibited cyclin E/CDK2, cyclin A/CDK2 and cyclin B/CDK2 complexes with $IC_{50}$'s approximately two-fold less than p27 alone (p16 itself not having any significant inhibitory activity against any of the three complexes).

Other aspects of the present invention include: preparations of the subject chimeric proteins; expression constructs for recombinant production of the subject chimeric proteins, particularly for use as part of a gene therapy treatment; and methods for modulating cell proliferation and/or differentiation with the subject chimeric proteins.

For convenience, certain terms employed in the specification, examples, and appended claims are collected here.

The phrase "CDK-binding motif" refers to that portion of a protein which interacts either directly or indirectly with a cyclin dependent kinase (CDK). The binding motif may be a sequential portion of the protein, i.e., a contiguous sequence of amino acids, or it may be conformational, i.e. a combination of non-contiguous sequences of amino acids which, when the protein is in its native folding state, forms a structure which interacts with a CDK. The term "CDK-binding motif" explicitly includes any polypeptide which is identical, substantially homologous, or otherwise functionally or structurally equivalent to a portion of a CKI protein which binds directly or indirectly to a CDK or CDK complex. Other exemplary CDK-binding motifs can be provided from, for example, Rb and Rb-like proteins as well as cyclins.

An "inhibitor of CDK activation" refers to a molecule able to interact with a CDK and prevent activation of a kinase activity of the CDK either by, for example, inhibiting formation of CDK complexes including regulatory subunits, inhibiting interaction of the CDK subunit with activating kinases or phosphatases, inhibiting substrate binding, inhibiting ATP binding, and/or inhibiting conformational changes required for enzymatic activity. Accordingly, such inhibition may be by a direct, competitive mechanism, or by an indirect, non- or uncompetitive mechanism.

As used herein, the term "CKI protein" refers to a protein which can bind to and inhibit activation of a cyclin dependent kinase. Exemplary CKI proteins include members of the INK4 family, such as $p16^{INK4A}$ or $p15^{INK4B}$, and members of the CIP family, such as $p21^{CIP1}$, $p27^{KIP1}$, and $p57^{KIP2}$.

The term "INK4 protein" refers to a family of structurally related CDK inhibitors characterized by a fourfold repeated ankyrin-like sequence (Elledge et al. (1994) Curr. Opin. Cell Biol. 6:874–878), and the ability to bind to CDKs, especially CDK4 and CDK6. Exemplary members of this protein family include p16 (INK4A/MTS1; Serrano et al (1993) Nature 366:704–707); p15 (INK4B; Hamnon et al. (1994) Nature 371:257–261); p18 (Guan et al. (1994) Genes Der. 8:2939–2952) and p19 (Chan et al. (1995) Mol. Cell Biol. 15:2682–2688; and Hirai et al. (1995) Mol. Cell Biol. 15:2672–2681). Other proteins have been identified in the art as having tandemly arranged ankyrin-like sequences, such as the Pho81p protein (Ogawa et al. (1995) Mol. Cell Biol. 15:997–1004), and may provide CDK-binding motifs which are functionally equivalent to those of an INK4 protein.

The term "CIP protein" refers to members of another CKI protein family which includes $p21^{CIP1}$ (WAF1/SDI1/CAP20; Xiong et al. (1983) Nature 36:701–704); $p27^{KIP1}$ (Polyak et al. (1994) cell 78:67–74); and $p57^{KIP2}$ (Lee et al. (1995) Genes Dev. 9:639–649; and Matsuoka et al. (1995) Genes Dev. 9:650–662). In addition to the functional characteristic of CDK inhibition, the CIP proteins each have a CDK inhibitory motif (a CDK-binding motif) of about 50 amino acids, referred to herein as a "p21/p27" inhibitory domain, which is conserved in members of the CIP family, as well as, for example, members of the Rb-like protein family.

A "chimeric protein" refers to a protein which includes polypeptide sequences from at least two different and distinct proteins. A chimeric protein can be a fusion protein, or the different polypeptide sequences can be covalently linked by a non-peptide bond, e.g., a cross-linking agent.

As used herein, the term "fusion protein" is art recognized and refer to a chimeric protein which is at least initially expressed as single chain protein comprised of amino acid sequences derived from two or more different proteins, e.g., the fusion protein is a gene product of a fusion gene.

The art term "fusion gene" refers to a nucleic acid in which two or more genes are fused resulting in a single open reading frame for coding two or more proteins that as a result of this fusion are joined by one or more peptide bonds.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding a fusion polypeptide of the present invention, including both exonic and (optionally) intronic sequences. An exemplary recombinant gene encoding a subject fusion protein is represented by SEQ. ID No: 1.

As used herein, the term "transfection" means the introduction of a heterologous nucleic acid, e.g., an expression vector, into a recipient cell by nucleic acid-mediated gene transfer. "Transformation", as used herein with respect to transfected nucleic acid, refers to a process in which a cell's genotype is changed as a result of the cellular uptake of exogenous DNA or RNA, and, for example, the transformed cell expresses a recombinant form of a CDK-inhibitory fusion polypeptide of the present invention.

"Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a fusion protein of the present invention) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

"Transcriptional regulatory sequence" is a generic term used throughout the specification to refer to DNA sequences, such as initiation signals, enhancers, and promoters and the like which induce or control transcription of protein coding sequences with which they are operably linked. In preferred embodiments, transcription of the fusion gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of one of the naturally-occurring forms of a CDK inhibitor protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well.

"Operably linked" when describing the relationship between two DNA regions simply means that they are functionally related to each other. For example, a promoter or other transcriptional regulatory sequence is operably linked to a coding sequence if it controls the transcription of the coding sequence.

"Recombinant host cells" refers to cells which have been transformed or transfected with vectors constructed using recombinant DNA techniques. As relevant to the present invention, recombinant host cells are those which produce CDK inhibitor fusion proteins by virtue of having been transformed with expression vectors encoding these proteins.

As used herein, a "transgenie animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a CDK inhibitory fusion promin. The term "chimeric animal" is used herein to refer to animals in which the recombinant gene is found, or in which the recombinant is expressed in some but not all cells of the animal. The term "tissue-specific chimeric animal" indicates that the recombinant gene is present and/or expressed in some tissues but not others.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

One aspect of the invention pertains to a nucleic acid having a nucleotide sequence encoding a chimeric CDK inhibitor protein, and/or equivalents of such nucleic acids. In general, the nucleic acid is derived by the in-frame fusion of coding sequences from two or more proteins which have CDK-inhibitory motifs, such motifs being preserved in the resultant chimeric protein. Accordingly, such chimeric proteins can be derived to include, for example, CKI promin sequences, such as from INK4 or CIP proteins. For instance, as described in the appended examples, a coding sequence providing the CDK-binding motif of an INK4 promin can be fused in frame to a coding sequence providing a CDK-binding motif of a CIP promin.

Exemplary nucleic acid of the present invention encode fusion proteins which include at least a CDK-binding portion of an INK4 protein, such as p15, p16, p18 or p19. In preferred embodiments, the chimeric promin includes at least the two ankyrin-like sequence of the C-terminal portion of the INK4 protein, e.g. corresponding to the $3^{rd}$ request (residues 69–101) and $4^{th}$ repeat (residues 102–133) of $p16^{INK4A}$ (see Serrano et al. (1993) 366:704–707).

Similarly, preferred chimeric proteins of the present invention include at least the p21/27-related inhibitory domain of a CIP protein, e.g. from p21, p27 or p57. For example, the chimeric protein can include the CDK-inhibitory motif corresponding to residues 28–79 of p27, residues 17–68 of p21, and/or residues 31–82 of p57, though larger fragments may be used such as described in the appended examples.

Moreover, CDK-binding motifs homologous to those occurring in either the INK4 or CIP protein families have been observed in other proteins. For example, the p21/p27-related inhibitory domain typical of the CIP protein family has been identified in such other proteins as the Rb-related protein p107 (Zhu et al. (1995) Genes Der 9:1740–1752). Likewise, ankyrin-like repeats homologous with the INK4 proteins have been identified in such other proteins as the Pho81p protein (Ogawa et al. (1995) Mol Cell Biol 15:997–1004). Consequently, it will be apparent to one of ordinary skill in the art, based on the disclosure herein, that functional equivalents of the INK4 and CIP proteins, e.g. which are capable of binding to a CDK and inhibiting kinase activation, exist and can be provided in the subject chimeric proteins.

Furthermore, it will be understood that the subject chimeric proteins can include CDK-binding motifs from proteins unrelated to either the INK4 family or CIP family. Moreover, such CDK-binding motifs, while inhibitory in and of themselves, can be derived from proteins which are otherwise activating in their full length form. To illustrate, the subject chimeric protein can be generated with a fragment of a cyclin which retains its CDK binding ability but not the CDK activating ability characteristic of the full length protein. In some instances it may be necessary to introduce an unstructured polypeptide linker region between portions of the chimeric protein derived from different proteins. This linker can facilitate enhanced flexibility of the chimeric protein allowing the CDK-binding motifs from each portion to freely and (optionally) simultaneously interact with a CDK by reducing steric hindrance between the two fragments, as well as allowing appropriate folding of each portion to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. Nos. 5,091,513 and 5,258,498. Naturally occurring unstructured linkers of human origin are preferred as they reduce the risk of immunogenicity.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a fusion gene sequence (see, for example, Current Protocols in Molecular Biology, eds. Ausubel et al. John Wiley & Sons: 1992).

The term nucleic acid as used herein is intended to include nucleotide sequences encoding functionally equivalent chimeric proteins which, for example, retain the ability to bind to a cyclin-dependent kinase. Equivalent nucleotide sequences will include sequences that differ by one or more nucleotide substitutions, additions or deletions, such as allelic variants; and will, therefore, include sequences that differ from the nucleotide sequence of, for example, an INK4 or CIP gene known in the art due to the degeneracy of the genetic code. Equivalents will also include nucleotide sequences that hybridize under stringent conditions (i.e., equivalent to about 20°–27° C. below the melting temperature ($T_m$) of the DNA duplex formed in about 1 M salt) to the nucleotide sequence encoding a naturally-occurring CDK-binding motif. Furthermore, equivalent nucleic acids will include those with nucleotide sequences which differ from the natural sequence which encodes a CDK-binding motif because of degeneracy in the genetic code. For example, a number of amino acids are designated by more than one triplet. Codons that specify the same amino acid can, accordingly, be used to replace codons in the naturally-occurring sequence.

This invention also provides expression vectors comprising a nucleotide sequence encoding a subject CDK inhibitor chimeric protein and operably linked to at least one regulatory sequence. Regulatory sequences are art-recognized and are selected to direct expression of the fusion protein. Accordingly, the term regulatory sequence includes promoters, enhancers and other expression control elements. Exemplary regulatory sequences are described in Goeddel; Gene Expression Technology: Methods in Enzymology 185, Academic Press, San Diego, CA (1990). For instance, any of a wide variety of expression control sequences-sequences that control the expression of a DNA sequence when operatively linked to it may be used in these vectors to express DNA sequences encoding the fusion proteins of this invention. Such useful expression control sequences, include, for example, the early and late promoters of SV40, adenovirus or cytomegalovirus irranediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. Of course, the transcriptional regulatory sequences can include those sequences which naturally control expression of one of the genes used to derive the fusion protein, such as 5' flanking sequences of an INK4 or CIP gene.

It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

Expression vehicles for production of recombinant forms of the subject chimeric proteins include plasmids and other vectors. For instance, suitable vectors for expression of a fusion protein of the present invention include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors (other than for gene therapy) contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells.

In some instances, it may be desirable to express the subject fusion protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

Another aspect of the present invention concerns preparations of the subject chimeric proteins. In particular, purified and semi-purified preparations of the CDK inhibitors can be formulated according to specifications attendant the desired use of the chimeric protein.

With respect to purifying the subject chimeric proteins, Applicant notes that it is widely appreciated that addition of certain heterologous sequences to a protein can facilitate the expression and purification of the proteins. For example, a fusion promin of the present invention can be generated to also include a glutathione-S-transferase (GST) polypeptide sequence. The GST portion of the recombinant proteins can enable easy purification of the protein, such as by the use of glutathione-derivativized matrices (see, for example, Current Protocols in Molecular Biology, eds. Ausabel et al. (N.Y.: John Wiley & Sons, 1991)). In another embodiment, the subject fusion protein can also include a purification leader sequence, such as a poly-(His)/enterokinase cleavage site sequence located at the N-terminus of the subject fusion protein. Such sequences facilitates purification of the poly (His)-expressed fusion protein by affinity chromatography using a $Ni^{2+}$ metal resin. The purification leader sequence can then be subsequently removed by treatment with enterokinase (e.g., see Hochuli et al. (1987) J. Chromatography 411:177; and Janknecht et al. PNAS 88:8972).

The present invention further pertains to methods of producing the subject chimeric proteins. For example, a host cell transfected with a nucleic acid vector directing expression of a nucleotide sequence encoding one of the chimeric proteins of the present invention can be cultured under appropriate conditions to allow expression of the polypeptide to occur. The peptide may be secreted and isolated from a mixture of host cells and medium by inclusion of a signal secretion sequence. Alternatively, the peptide may be retained cytoplasmically and the cells harvested, lysed and the protein isolated. A cell culture includes host cells, media and other byproducts. Suitable media for cell culture are well known in the art. The recombinant chimeric promin can be isolated from cell culture medium, host cells, or both using techniques known in the art for purifying proteins including ion-exchange chromatography, gel filtration chromatography, ultrafiltration, electrophoresis, and immuno-affinity purification with antibodies specific for portions of the chimeric protein.

This invention also pertains to a host cell transfected to recombinantly express one of the subject chimeric proteins. The host cell may be any prokaryotic or eukaryotic ell. Thus, a nucleic acid derived from the fusion of coding sequences for two or more CDK-binding motifs from different proteins can be used to produce a recombinant form of the chimeric protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g., p16, p21, p27, p57, p107, cyclins and the like. Similar procedures, or modifications thereof, can be employed to prepare recombinant chimeric proteins by microbial means or tissue-culture technology in accord with the subject invention.

The chimeric molecules of the present invention can also be generated using well-known cross-linking reagents and protocols. For example, there are a large number of chemical cross-linking agents that are known to those skilled in the art and useful for cross-linking two heterologous polypeptide chains. For the present invention, the preferred cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art. These include: succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminebenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl- a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoato (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vive.

In addition to the heterobifunctional cross-linkers, there exists a number of other cross-linking agents including homobifunctional and photoreactive cross-linkers. Disuccinimidyl substrate (DSS), bismaleimidohexane (BMH) and dimethylpimelimidate 2 HCl (DMP) are examples of useful homobifunctional cross-linking agents, and bis-[β-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this invention. For a recent review of protein coupling techniques, see Means et al. (1990) Bioconjugate Chemistry 1:2–12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

The reaction buffer should be free of extraneous amines and sulfhydryls. The pH of the reaction buffer should be 7.0–7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the protein chosen for reaction with maleimides, activated halogens, or pyridyl disulfides must contain a free sulfhydryl, usually from a cysteine residue. Free sulfhydryls can be generated by reduction of protein disulfides. Alternatively, a primary amine may be modified with Traut's Reagent to add a sulfhydryl (Blattler et al. (1985) Biochem 24:1517, incorporated by reference herein). Again, Ellman's Reagent can be used to calculate the number of sulfhydryls available in protein.

In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with -SH groups at slightly acidic to neutral pH ranges (6.5–7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing protein under the appropriate buffer conditions. The protein-protein conjugates can be isolated from the reaction mixture by methods such as gel filtration or by dialysis.

For certain of the therapeutic uses of the subject chimeric proteins, particularly cutaneous uses such as for the control of keratinocyte proliferation, direct administration of the protein will be appropriate (rather than use of a gene therapy construct). Accordingly, the subject chimeric protein, or a pharmaceutically acceptable salt thereof, may be conveniently formulated for administration with a biologically acceptable medium, such as water, buffered saline, polyol (for example, glycerol, propylene glycol, liquid polyethylene glycol and the like) or suitable mixtures thereof. In preferred embodiments, the chimeric protein is dispersed in lipid formulations, such as miscelles, which closely resemble the lipid composition of natural cell membranes to which the chimeric protein is to be delivered.

The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the chimeric protein, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985).

In an exemplary embodiment, the chimeric protein is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the proteins of the invention are formulated into ointments, salves, gels, or creams as generally known in the art.

Yet another aspect of the invention pertains to methods of treating proliferative and/or differentiative disorders which arise from cells which, despite aberrant growth control, still require one or more CDKs (e.g., CDK4 or CDK6) for cell growth. There are a wide variety of pathological cell proliferative conditions for which the fusion gene constructs of the present invention can provide therapeutic benefits, with the general strategy being the inhibition of an anomalous cell proliferation. For instance, the gene constructs of the present invention can be used as a part of a gene therapy protocol in a cell in which a cell-cycle regulatory protein (such as an INK4 or CIP protein) is misexpressed or in which signal transduction pathways upstream of the protein are dysfunctional. To illustrate, cell types which exhibit pathological or abnormal growth presumably dependent at least in part on a function of a, INK4 or CIP protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from, for example, de-differentiation of tissue which may (optionally) be accompanied by abortive reeentry into mitosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors. It will also be apparent that, by transient use of gene therapy constructs of the subject fusion proteins, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For example, the subject CDK inhibitors can be employed therapeutically as part of a regimen to regulate organs after physical, chemical or pathological insult.

Furthermore, as described in the art, transformation of a cell can be due in part to a loss-of-function mutation to a particular INK4 gene, e.g., ranging from a point mutation to gross deletion of the gene. Additionally, other data suggests that certain disorders may arise because cells have lost the ability to induce expression of an INK4 gene. Normal cell proliferation, for instance, is generally marked by responsiveness to negative autocrine or paracrine growth regulators, such as members of the TGF-β family, e.g. TGF-β1, TGF-β2 or TGF-β3, and related polypeptide growth inhibitors. Ordinarily, control of cellular proliferation by such growth regulators, particularly in epithelial and hemopoietic cells, is in the form of growth inhibition. Moreover, as described in Harmon and Beach (1995) Nature 371:257–261, TGF-β inhibits cell proliferation by inducing expressions of p15, which in turn inhibits activation of CDK4 or CDK6 complexes.

It has been observed that a significant percentage of human cancers derived from cells types ordinarily inhibited by TGF-β display a reduced responsiveness to this growth regulator. For instance, some tumors of colorectal, liver epithelial, and epidermal origin show reduced sensitivity and resistance to the growth-inhibitory effects of TGF-β as compared to their normal counterparts. In this context, a noteworthy characteristic of several retinoblastoma cell lines is the absence of detectable TGF-β receptors. Treatment of such tumors with the subject fusion proteins provides an opportunity to mimic the TGF-β inhibitory signal. Moreover, it will be appreciated that the subject method can be used generally to inhibit proliferation of cells which, in general, are still reliant on cyclin dependent kinases.

In accordance with the subject method, expression constructs of the subject fusion proteins may be administered in any biologically effective carrier, e.g. any formulation or composition capable of effectively transfecting cells in vivo with a recombinant fusion gene. Approaches include insertion of the subject fusion gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject fusion proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding one of the subject CCR-proteins, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad Sci. USA 85:6460–6464; Wilson et al. (1988) Proc. Natl. Acad. Sci. USA 85:3014–3018; Armentano et al. (1990) Proc. Natl. Acad Sci. USA 87:6141–6145; Huber et al. (1991) Proc. Natl. Acad Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject fusion proteins, it is important to note that a prerequisite for the successful infection of target cells by most retroviruses, and therefore of stable introduction of the recombinant gene, is that the target cells must be dividing. In general, this requirement will not be a hindrance to use of retroviral vectors to deliver the subject fusion gene constructs. In fact, such limitation on infection can be beneficial in circumstances where the tissue (e.g. nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) PNAS 86:9079–9083; Julan et al. (1992) J. Gen Virol 73:3251–3255; and Goud et al. (1983) Virology 163:251–254); or coupling cell surface ligands to the vital env proteins (Neda et al. (1991) J Biol Chem 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue-or cell-specific transcriptional regulatory sequences which control expression of the fusion gene of the retroviral vector.

Another viral gene delivery system useful in the present invention utilitizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) BioTechniques 6:616; Rosenfeld et al. (1991) Science 252:431–434; and Rosenfeld et al. (1992) Cell 68:143–155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes Herz and Gerard (1993) Proc. Natl. Acad Sci. USA 90:2812–2816) and muscle cells (Quantin et al. (1992) Proc. Natl. Acad Sci. USA 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et at., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in *Methods in Molecular Biology*, E. J. Murray, Ed. (Humana, Clifton, NJ, 1991) vol. 7. pp. 109–127). Expression of the inserted fusion gene can be under control of, for example, the E1A promoter, the major late promoter (MLP) and associated leader sequences, the E3 promoter, or exogenously added promoter sequences.

Yet another viral vector system useful for delivery of the subject fusion gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

Other viral vector systems that may have application in gene therapy have been derived from herpes virus, vaccinia virus, and several RNA viruses. In particular, herpes virus vectors may provide a unique strategy for persistent expression of the subject fusion proteins in cells of the central nervous system and ocular tissue (Pepose et al. (1994) Invest Ophthalmol Vis Sci 35:2662–2666)

In addition to viral transfer methods, such as those illustrated above, non-viral methods can also be employed to cause expression of a the subject fusion proloins in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding one of the subject fusion proteins can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al. (1992) Neurol. Med. Chir. 32:873–876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, the subject gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via receptor-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) Science 260–926; Wagner et al. (1992) PNAS 89:7934; and Christiano et al. (1993) PNAS 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drags, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, Concise Encyclopedia of Medical & Dental Materials, ed. by David Williams (MIT Press: Cambridge, MA, 1990); and the Sabel et al. U.S. Pat. No. 4,883,666. In another embodiment of an implant, a source of cells producing the recombinant virus is encapsulated in implantable hollow fibers. Such fibers can be pre-spun and subsequently loaded with the viral source (Aebischer et al. U.S. Pat. No. 4,892,538; Aebischer et al. U.S. Pat. No. 5,106,627; Hoffman et al. (1990) Expt. Neurobiol. 110:39–44; Jaeger et al. (1990) Prog. Brain Res. 82:41–46; and Aebischer eta. (1991) J. Biomech. Eng. 113:178–183), or can be co-extruded with a polymer which acts to form a polymeric coat about the vital packaging cells (Lim U.S. Pat. No. 4,391,909; Sefton U.S. Pat. No. 4,353,888; Sugamori et al. (1989) Trans. Am. Artif. Intern. Organs 35:791–799; Sefton eta. (1987) Biotechnol. Bioeng. 29:1135–1143; and Aebischer eta. (1991) Biomaterials 12:50–55). Again, manipulation of the polymer can be carried out to provide for optimal release of viral particles.

To further illustrate the use of the subject method, the therapeutic application of a CDK inhibitor fusion protein, e.g., by gene therapy, can be used in the treatment of a neuroglioma. Gliomas account for 40–50% of intracranial tumors at all ages of life. Despite the increasing use of radiotherapy, chemotherapy, and sometimes immunotherapy after surgery for malignant glioma, the mortality and morbidity rates have not substantially improved. However, there is increasing experimental and clinical evidence that for a significant number of gliomas, loss of TGF-$\beta$ responsiveness is an important event in the loss of growth control. Irrespective of the cause of decreased responsiveness, e.g. the loss of function of p15 or the loss of other TGF-$\beta$ signal transduction proteins, exogenous expression of, for example, an INK4 fusion protein such as p15/p27 fusion protein in the cell can used effectively to inhibit cell proliferation.

It has been demonstrated that gene therapy can be used to target glioma cells for expression of recombinant proteins (Miyao et al. (1993) J. Neurosci. Res. 36:472–479; Chen et al. (1994) PNAS 91:3054–3057; and Takamiya et al. (1993) J. Neurosurg. 79:104–110). Thus, a gene construct for expressing the subject fusion protein can be delivered to the tumor, preferably by sterotactic-dependent means. In preferred embodiments, the gene delivery system is a retroviral vector. Since rapidly growing normal cells are rare in the adult CNS, glioma cells can be specifically transduced with a recombinant retrovirus. For example, the retroviral particle can be delivered into the tumor cavity through an Ommaya tube after surgery, or alternatively, packaging fibroblasts encapsulated in retrievable immunoisolatory vehicles can be introduced into the minor cavity. In order to increase the effectiveness and decrease the side effects of the retrovirus-mediated gene therapy, glioma-specific promoters can be used to regulate expression of the therapeutic gene. For example, the promoter regions of glial fibrillary acidic protein (GFAP) and myelin basis protein (MBP) can operably linked to the fusion gene in order to direct glial cell-specific expression of the fusion protein.

In another embodiment, gene therapy can be used in conjunction with the subject fusion proteins in the treatment of various carcinomas. In a representative embodiment, a gene therapy system comprising the subject fusion gene is used to treat certain breast cancers. In preferred embodiments, expression of the subject fusion protein is controlled at least in part by a mammary-specific promoter, a number of which are available (for review, see Hermighausen (1990) Protein Expression and Purification 1:3–8; and Gtinzberg et al. (1992) Biochern J 283:625–632).

In similar fashion, gene therapy protocols involving delivery of the subject fusion promin can be used in the treatment of malignant melanoma, which also serves as a model for progressive TGF-$\beta$ resistance in transformation. In preferred embodiments, gene therapy protocols for treatment of melanomas include, in addition to the delivery of the fusion gene construct, the delivery of a pharmaceutical preparation of the gene by direct injection. For instance, U.S. Pat. No. 5,318,514 describes an applicator for the electroporation of genes into epidermal cells and can be used in accordance with the present invention.

The subject fusion proteins can be used in the treatment of hyperproliferative vascular disorders, e.g. smooth muscle hyperplasia (such as atherosclerosis) or restinosis, as well as other disorders characterized by fibrosis, e.g. rheumatoid arthritis, insulin dependent diabetes mellitus, glomemlonephritis, cirrhosis, and scleroderma, particularly proliferative disorders in which loss of TGF-$\beta$ autotrine or paracrine signaling, and accordingly loss of p15 function, is implicated.

For example, restinosis continues to limit the efficacy of coronary angioplasty despite various mechanical and pharmaceutical interventions that have been employed. An important mechanism involved in normal control of intimal proliferation of smooth muscle cells appears to be the induction of autotrine and paracrine TGF-β inhibitory loops in the smooth muscle cells (Scott-Burden et al. (1994) Tex Heart Inst J 21:91–97; Graiger et al. (1993) Cardiovasc Res 27:2238–2247; and Grainger et al. (1993) Biochem J294:109–112). Loss of sensitivity to TGF-β, or alternatively, the overriding of this inhibitory stimulus such as by PDGF autostimulation, can be a contributory factor to abnormal smooth muscle proliferation in restinosis. It may therefore be possible to treat or prevent restinosis by the use of gene therapy with CDK inhibitor fusion promin of the present invention. The fusion gene construct can be delivered, for example, by percutaneous transluminal gene transfer (Mazur et al. (1994) Tex Heart Inst J 21:104–111) using viral or liposomal delivery compositions. An exemplary adenovirus-mediated gene transfer technique and compositions for treatment of cardiac or vascular smooth muscle is provided in PCT publication WO 94/11506.

Transforming growth factor-β is also understood to play a significant role in local glomerular and interstitial sites in human kidney development and disease. Consequently, the subject method provides a method of treating or inhibiting glomerulopathies and other renal proliferative disorders comprising the in vivo delivery and recombinant expression of the subject fusion proteins in kidney tissue.

The subject method can also be used to treat retinoblastomas in which the retinoblastoma gene (RB) is not itself impaired, e.g. the effective impairment of the RB checkpoint is the result of a failure to control CDK4 phosphorylation of RB. Thus, one of the subject fusion proteins can be expressed in a retinoblastoma cell, thereby causing inhibition of CDK4 activation and down-regulating RB phosphorylation. To illustrate, a recombinant retrovirus can be constructed to facilitate expression of a fusion protein including an INK4 protein, e.g., derived from p16 or p15, and a CIP protein, e.g., derived from p21, p27 or p57. Infectivity of retinoblastoma cells can be enhanced by derivatizing the env protein with antibodies specific for retinoblastoma cells, e.g. antibodies to retinal S-antigen (Doroso et al. (1985) Invest Opthalmol Vis Sci 26:560–572; see also Liao et al. (1981) Eur J Immunol 11:450–454; and U.S. Pat. No. 4,444,744).

In yet another embodiment, the subject gene is delivered to a sarcoma, e.g. an osteosarcoma or Kaposi's sarcoma. In a representative embodiment, the gene is provided in a viral vector and delivered by way of a viral particle which has been derivatized with antibodies immunoselective for an osteosarcoma cell (see, for example, U.S. Pat. Nos. 4,564, 517 and 4,444,744; and Singh et al. (1976) Cancer Res 36:4130–4136).

Given the role of CDK activation in various epithelial cell proliferative disorders, it will be evident that the subject fusion proteins will find ready application for the treatment or prophylaxis of, for example, psoriasis; keratosis; acne; comedogenic lesions; verrucous lesions such as verruca plana, plantar warts, verruca acaminata, and other verruciform lesions marked by proliferation of epithelial cells; folliculitis and pseudofolliculitis; keratoacanthoma; callosities; Darier's disease; ichthyosis; lichen planus; molluscous contagiosum; melasma; Fordyce disease; and keloids or hypertrophic scars.

Yet another aspect of the present invention relates to the use of the subject fusion proteins to control hair growth. The growth of hard keratin fibers such as wool and hair is dependent on the proliferation of derreal sheath cells. Hair follicle stem cells of the sheath are highly active, and give rise to hair fibers through rapid proliferation and complex differentiation. The hair cycle involves three distinct phases: anagen (growing), catagen (regressing), and telogen (resting). The epidermal stem bells of the hair follicle are activated by dermal papilla during late telogen. This is termed "bulge activation". Moreover, such stem cells are thought to be pluripotent stem cells, giving rise not only to hair and hair follicle structures, but also the sebaceous gland and epidermis. The subject method provides a means for altering the dynamics of the hair growth cycle to induce quiescence of proliferation of hair follicle cells, particularly stem cells of the hair follicle, inhibiting CDK activation.

For instance, gene therapy treatments or, alternatively, topical administration of a fusion protein preparation, can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, the subject fusion proteins can be used to manage hirsutism, a disorder marked by abnormal hairiness. Application of the CDK inhibitors of the present invention can also provide a process for extending the duration of depilation.

Moreover, because the CDK inhibitor fusion proteins are likely to be cytostatic to epithelial cells, rather than cytotoxic, these proteins can be used to protect hair follicle cells from cytotoxic agents which require progression into S-phase of the cell-cycle for efficacy, e.g. radiation-induced death. Treatment with a CDK inhibitor of the present invention provides protection by causing the hair follicle cells to become quiescent, e.g., by inhibiting the cells from entering S phase, and thereby preventing the follicle cells from undergoing mitotic catastrophe or programmed cell death. For instance, such treatments can be used for patients undergoing chemo- or radiation-therapies which ordinarily result in hair loss.

The subject method can also be used in the treatment of folliculitis, such as folliculitis decalvans, folliculitis ulerythematosa reticulata or keloid folliculitis. For example, a cosmetic prepration of an CDK inhibitory fusion protein can be applied topically in the treatment of pseudofolliculitis, a chronic disorder occurring most often in the submandibular region of the neck and associated with shaving, the characteristic lesions of which are erythematous papules and pustules containing buried hairs.

In similar fashion, such preparations can be used in the treatment of granulomas, e.g. tumor-like mass or nodule of granulation tissue, which may include epithelial tissue derived from cutaneous or mucosal sources.

In another aspect of the invention, the subject method can be used in conjunction with various periodontal procedures in which inhibition of epithelial cell proliferation in and around periodontal tissue is desired. For example, preparations of the present invention can find application in the treatment of peridontal disease. It is estimated that in the United States alone, there are in excess of 125 million adults with periodontal disease in varying forms. Periodontal disease starts as inflammatory lesions because of specific bacteria localizing in the area where the gingiva attaches to the tooth. Usually first to occur is a vascular change in the underlying connective tissue. Inflammation in the connective tissue stimulates the following changes in the epithelial lining of the sulcus and in the epithelial attachment: increased milotic activity in the basal epithelial layer; increased producing of keratin with desquamation; cellular desquamation adjacent to the tooth surface tends to deepen the pocket; epithelial cells of the basal layer at the bottom of the sulcus and in the area of attachment proliferate into the connective tissue and break up of the gingival fibers begins to occur, wherein dissolution of the connective tissue results in the formation of an open lesion. The application of CDK inhibitor preparations to the periodontium can be used to inhibit proliferation of epithelial tissue and thus prevent further periodontoclastic development.

In yet another embodiment of the present invention, the subject CDK inhibitors can be used to inhibit spermatogenesis or oogenesis by inhibiting progression through mitotic or meiotic cell-cycle stages. The anti-mitotic and/or anti-meiotic activity of the fusion proteins identified in the present invention may accordingly be used, for example, in birth control methods by disrupting oogenic pathways in order to prevent the development of either the egg or sperm, or by preventing milotic progression of a fertilized egg.

In a still further embodiment, the subject fusion protein is recombinantly expressed in tissue which is characterized by unwanted de-differentiation and which may also be undergoing unwanted apoptosis. For instance, many neurological disorders are associated with degeneration of discrete populations of neuronal elements. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Many are age-related, occurring in far greater incidence in older people than in younger. Several of these are degenerative diseases characterized by the death of neurons in various parts of the central nervous system, especially the cerebral cortex. However, some forms of dementia are associated with degeneration of the thalamus or the white matter underlying the derebral cortex. Here, the cognitive dysfunction results from the isolation of cortical areas by the degeneration of efferents and afferents. Huntington's disease involves the degeneration of intrastriatal and cortical cholinergic neurons and GABAergic neurons. Pick's disease is a severe neuronal degeneration in the neocortex of the frontal and anterior temporal lobes, sometimes accompanied by death of neurons in the striatum. Accordingly, the subject fusion proteins can be delivered to the effected tissue by gene therapy techniques. It is noted that numerous advances have been made in the construction of expression vectors, cellular and viral transgene carriers, and the characterization of target cells for neuronal gene therapy, and can be readily adapted for delivery of the subject genes (see, for example, Suhr et al. (1993) Arch Neurol 50:1252–1268; Jiao et al. (1993) Nature 362:450–453; Friedmann (1992) Ann Meal24:411–417; and Freese et al. (1991) Nuc Acid Res 19:7219–7223)

In addition to degenerative-induced dementias, the subject gene therapy systems can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Gulllaln-Barre syndrome and chronic peripheral neuropathy, as well as other diseases which can be manifest as progressive bulbar palsies or spinal muscular atrophies. Moreover, the use of the subject fusion gene therapy constructs is amenable to the treatment of disorders of the cerebellum which result in hypotonia or ataxia, such as those lesions in the cerebellum which produce disorders in the limbs ipsilateral to the lesion. For instance, p16/p27 fusion gene constructs can used to treat a restricted form of cerebellar cortical degeneration involving the anterior lobes (vermis and leg areas) such as is common in alcoholic patients.

Furthermore, the subject fusion proteins can also be used in the treatment of autonomic disorders of the peripheral nervous system, which include disorders affecting the innervation of smooth muscle and endocrine tissue (such as glandular tissue). For instance, recombinant fusion protein of the present invention can be expressed by gene therapy and used to treat tachycardia or atrial cardiac arrythmias which may arise from a degenerative condition of the nerves innervating the striated muscle of the heart.

As will be apparent, the subject gene constructs can be used to cause expression of the fusion polypeptides in cells propagated in culture, e.g. to produce proteins or polypeptides, including fusion proteins or polypeptides, for purification. In addition, recombinant expression of the subject fusion polypeptides in cultured cells can be useful for controlling differentiation states of cells in vitro, for instance, by controlling the level of activation of a CDK. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration. By preventing the activation of one or more CDKs, particularly in $G_0$ or G1, certain of the subject fusion proteins can prevent mitotic progression and hence provide a means for ensuring an adequately restrictive environment in order to maintain neuronal cells at various stages of differentiation, and can be employed, for instance, in cell cultures designed to test the specific activities of trophic factors. Other tissue culture systems which require maintenance of differentiation will be readily apparent to those skilled in the art. In this respect, each of the subject antagonist of CDK4 activation can be used for ex vivo tissue generation, as for example, to enhance the generation of prosthetic tissue devices for implantation. That is, by inhibiting the activation of a CDK with one of the subject fusion proteins, cultured cells can be guided along certain differentiative pathways.

Exemplification

The invention now being generally described, it will be more readily understood by reference to the following examples which are included merely for purposes of illustration of certain aspects and embodiments of the present invention, and are not intended to limit the invention.

A prototype embodiment of the CDK inhibitory fusion protein described above was derived from the fusion of the coding sequences from the human p27 and p16 cDNAs. The nucleotide sequence for the fusion gene encoding the p27- p16 protein is provided in SEQ ID No. 1, with the corresponding amino acid sequence being designated by SEQ ID No. 2. The construct includes a poly(His) leader for purification, along with a hinge region including a (Gly$_4$Ser)$_3$ linker to permit proper folding and breathing of each of the p27 and p16 portions of the resulting protein. The sequences for both human p27 and human p16 have been described in the art. Briefly, the p27-p16 fusion protein was constructed as follow.

The expression vector is p27-p16 from US Biocehmical. To construct the p27-p16 fusion, first we PCR amplified the p27 coding sequence using the following primers:
N-terminal primer: (SEQ ID No. 3) 5'-GCGGCCGGTCATATGCACCACCATCACCATCAC-TCAAACG-TGCGAGTGTCT-3' This primer carries an NdeI site and 6 histidine codons that are inserted between the ATG and the second amino acid of p27.
C-terminal primer: (SEQ ID No. 4) 5'-GCCGCCGGCGTCGACTCGGCCGAATTCGGATCC-ACCCCCGCCGGAACC-GCCACCCCCGCTGCCCCC-GCCACCCGTTTGACGTCTTCTGAGGCCAGG-3' This primer carries the (Gly$_4$Ser)$_3$ repeat and EcoR1, Sal1 and Hind3 restriction sites and eliminates the stop codon of p27.

The p27 PCR product was cut with NdeI and Hind3 and inserted into pT7-7 cut with NdeI and Hind3. The resulted construct was cut with EcoR1 and Sal1 and a full length p16 PCR product was inserted as an EcoR1-XhoI fragment. The position of the EcoR1 site allows the in-frame insertion of p16. The rest of the hinge region between the p27 and p16 coding sequences derives from the 5' end of the p16 cDNA.

The pT7p27-p16 expression plasmid was transformed into BL21 cells. For fusion protein expression, cells were grown in LB+50 µg/ml ampicillin at 37 C. to OD$_{600}$=0.8 and protein expression was induced by IPTG (fmal; conc.: 20 mM) for 4 hours as 37 C. Cells were collected and the pellet was frozen at –80 C. The preparation of the cell lysate and binding to a Ni$^{2+}$ charged sepharose resin (Invitrogen catalog no. RS01) was done according to the manufacturer's instruction (Invitrogen; see also Hochuli et al. (1987) J. Chromatography 411:177–184; and Janknecht et al. (1991) PNAS 88:8972–8976). The bound proteins were eluted with 50 mM, 200 mM, 350 mM, and 500 mM imidazol and the fractions were analyzed on SDS/PAGE. The 200 mM, 350 mM, and 500 mM imidazol fractions were collected, dialised against 1×PBS(1 mM KH$_2$PO$_4$, 10 mM Na$_2$HPO$_4$, 137 mM NaCl, 2.7 mM KCl, pH=7.4)+10% glycerol and stored at –80 C. in aliquots. ~25% of the rep was the fusion protein.

The purity of the p27-p16, p27, and p16 preparations were normalized using p16 and p27 specific antibodies.

The kinase inhibitory activity of the p27-p16 fusion protein was determined using an in vitro kinase assay in which the kinase activity of a particular cyclin/CDK complex was measured for varying concentrations of fusion protein. Briefly, the assay employs Sf9 cell extracts that were made from cells that were coinfected with the proper CDK and cyclin expression constructs. Typically, 44 µg of Sf9 extract in 50 µl of 50 mM Tris/Cl pH=7.6, 10 mM MgCl$_2$, 1 mM DTT, 25 pM ATP, 10 µCi $^{32}$P-γ-ATP was used in the absence of the presence of the particular inhibitor (inhibitor concentration was between 25nM to 1 µM). The reaction was carried out at 30° C. for 30 minutes using 2 µg of Gst-Rb as a substrate. Gst-Rb was recaptured Using GSH-agaraose, separated on 10% SDS/PAGE and stained with Comassie blue. After autoradiography the GST-Rb bands were cut out and $^{32}$P incorporation was measured.

The concentration of p27-p16 fusion protein at which 50% of the kinase activity was blocked (IC$_{50}$) was calculated for various cyclin/CDK pairs. The results are indicated in Table I.

TABLE I

| Inhibition of cyclin dependent kinase complexes by p27-p16 fusion protein | | | | |
|---|---|---|---|---|
| inhibitor | CDK4/cyclin D1 | CDK2/cyclin E | CDK2/cyclin A | cdc2/cyclin B |
| p27-p16 | 25 nm | 30 nm | 25 nm | 15 nm |
| p27 | 63 nm | 52 nm | 65 nm | 20 nm |
| p16 | 250 nm | >500 nm | >500 nm | >500 nm | nm = nanomolar

Moreover, the inhibition constant, K$_i$ for the inhibition of CDK4/cyclin D1 by p27-p16 fusion protein was determined to be 23 nm, compared to a K$_i$ of 75 nm for p16 inhibition of the same CDK4 complex.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A nucleic acid comprising a nucleotide sequence encoding a fusion polypeptide comprising CDK-biding motifs from two or more different proteins which bind to cyclin dependent kinases.

2. The nucleic acid of claim 1, wherein at least one of the CDK-binding motifs comprises tandemly arranged ankyrin-like sequences.

3. The nucleic acid of claim 1, wherein at least one of the CDK-binding motifs comprises p21/p27 inhibitory domain.

4. The nucleic acid of claim 1, which fusion polypeptide comprises a first CDK-binding motif and a second CDK-binding motif, the first and second CDK-binding motifs having different binding specificities, relative to one and other, for cyclin dependent kinases.

5. The nucleic acid of claim 1, which nucleic acid further comprises a transcriptional regulatory sequence operably linked to the nucleotide sequence encoding the fusion polypeptide.

6. The nucleic acid of claim 1, wherein at least one of the CDK-binding motifs is a CDK-binding motif of a CDK inhibitor protein.

7. The nucleic acid of claim 6, wherein the CDK inhibitor protein is an INK4 protein.

8. The nucleic acid of claim 7, wherein the INK4 protein is selected from the group consisting of p15, p16, p18 and p19.

9. The nucleic acid of claim 6, wherein the CDK inhibitor protein is a CIP protein.

10. The nucleic acid of claim 9, wherein the CIP protein is selected from the group consisting of $p21^{CIP1}$, $p27^{KIP1}$, and $p57^{KIP2}$.

11. The nucleic acid of claim 1, wherein the fusion polypeptide comprises a CDK-binding motif of p16, and a CDK-binding motif of $p27^{kip1}$.

12. The nucleic acid of claim 11, which nucleic acid comprises the $p16/p27^{kip1}$ coding sequence designated in SEQ ID No. 1.

13. A recombinant transfection system, comprising
(i) a gene construct including a nucleic acid encoding a fusion polypeptide comprising CDK-binding motifs from two or more different proteins which bind to cyclin dependent kinases, and operably linked to a transcriptional regulatory sequence for causing expression of the fusion polypeptide in eukaryotic cells, and
(ii) a gene delivery composition for transfecting a cell with the gene construct.

14. The recombinant transfection system of claim 13, wherein the gene delivery composition comprises a recombinant viral particle.

15. The recombinant transfection system of claim 13, wherein the gene delivery composition is selected from the group consisting of a liposome and a poly-cationic nucleic acid binding agent.

16. The recombinant transfection system of claim 13, wherein the gene delivery composition further comprises a pharmaceutically acceptable carrier.

17. The nucleic acid of claim 13, wherein at least one of the CDK-binding motifs comprises tandemly arranged ankyrin-like sequences.

18. The nucleic acid of claim 13, wherein at least one the CDK-binding motifs comprises p21/p27 inhibitory domain.

19. The nucleic acid of claim 13, which fusion polypeptide comprises a first CDK-binding motif and a second CDK-binding motif, the first and second CDK-binding motifs having different binding specificities, relative to one and other, for cyclin dependent kinases.

20. The recombinant transfection system of claim 13, wherein the gene construct comprises a viral vector.

21. The recombinant transfection system of claim 20, wherein the viral vector is an adenoviral vector.

22. The recombinant transfection system of claim 20, wherein the viral vector is an adeno-associated viral vector.

23. The recombinant transfection system of claim 20, wherein the viral vector is a retroviral vector.

24. The nucleic acid of claim 13, wherein at least one of the CDK-binding motifs is a CDK-binding motif of a CDK inhibitor protein.

25. The nucleic acid of claim 24, wherein the CDK inhibitor protein is an INK4 protein.

26. The nucleic acid of claim 25, wherein the INK4 protein is selected from the group consisting of p15, p16, p18 and p19.

27. The nucleic acid of claim 24, wherein the CDK inhibitor protein is a CIP protein.

28. The nucleic acid of claim 27, wherein the CIP protein is selected from the group consisting of $p21^{CIP2}$, $p27^{KIP1}$, and $p57^{KIP2}$.

29. The nucleic acid of claim 13, wherein the fusion polypeptide comprises a CDK-binding motif of p16, and a CDK-binding motif of $p27^{kip1}$.

30. The nucleic acid of claim 29, which nucleic acid comprises the $p16/p27^{kip1}$ coding sequence designated in SEQ ID No. 1.

31. A nucleic acid comprising a nucleotide sequence encoding a fusion polypeptide comprising a first CDK-binding motif comprising a polypeptide sequence having tandemly arranged ankyrin-like sequences, and a second CDK-binding motif comprising a polypeptide sequence having a p21/p27 inhibitory domain.

32. A nucleic acid comprising a nucleotide sequence encoding a fusion polypeptide comprising (i) a polypeptide sequence having a CDK-binding motif of an INK4 protein, and (ii) an polypeptide sequence having a CDK-binding motif of a CIP protein.

33. The nucleic acid of claim 32, wherein the INK4 protein is selected from a group consisting of p15, p16, p18 and p19.

34. The nucleic acid of claim 32, wherein the CIP protein is selected from the group consisting of $p21^{CIP1}$, $p27^{KIP1}$, and $p57^{KIP2}$.

35. A nucleic acid comprising a nucleotide sequence encoding a fusion polypeptide comprising (i) a CDK-binding motif of p16 or p15, and (ii) a p21/p27 inhibitory domain of $p21^{CIP1}$, $p27^{KIP1}$ or $p57^{KIP2}$.

36. A viral vector comprising a nucleotide sequence encoding a fusion polypeptide comprising CDK-binding motifs from two or more different proteins which bind to cyclin dependent kinases, which viral vector infects mammalian cells and expresses the fusion polypeptide.

37. An adenoviral vector comprising a nucleotide sequence encoding a fusion polypeptide comprising CDK-binding motifs from two or more different proteins which bind to cyclin dependent kinases.

* * * * *

UNITED STATES PATENT AND TRADEMARK OFFICE
CERTIFICATE OF CORRECTION

PATENT NO.     :     5,672,508

DATED          :     September 30, 1997

INVENTOR(S)    :     Jeno Gyuris, Lou Lamphere, David Beach

It is certified that error appears in the above-identified patent and that said Letters Patent is hereby corrected as shown below:

1. In column 33, lines 14-15, delete "and other" and insert therefor --another--.

2. In column 34, line 5, delete "and other" and insert therefor --another--.

Signed and Sealed this

Seventeenth Day of April, 2001

*Attest:*

NICHOLAS P. GODICI

*Attesting Officer*     *Acting Director of the United States Patent and Trademark Office*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1420 base pairs
( B ) TYPE: nucleic acid
( C ) STRANDEDNESS: both
( D ) TOPOLOGY: linear -continued (i i) MOLECULE TYPE: cDNA (i x) FEATURE:
  (A) NAME/KEY: CDS
  (B) LOCATION: 4..1176

(i x) FEATURE:
  (A) NAME/KEY: misc_feature
  (B) LOCATION: 4..24
  (D) OTHER INFORMATION: /label=POLY-HIS_TAG (x i) SEQUENCE DESCRIPTION: SEQ ID NO:1:

```
CAT ATG CAC CAC CAT CAC CAT CAC TCA AAC GTG CGA GTG TCT AAC GGG      48
    Met His His His His His His His Ser Asn Val Arg Val Ser Asn Gly
    1               5                   10                      15

AGC CCT AGC CTG GAG CGG ATG GAC GCC AGG CAG GCG GAG CAC CCC AAG      96
Ser Pro Ser Leu Glu Arg Met Asp Ala Arg Gln Ala Glu His Pro Lys
            20                  25                  30

CCC TCG GCC TGC AGG AAC CTC TTC GGC CCG GTG GAC CAC GAA GAG TTA     144
Pro Ser Ala Cys Arg Asn Leu Phe Gly Pro Val Asp His Glu Glu Leu
                35                  40                  45

ACC CGG GAC TTG GAG AAG CAC TGC AGA GAC ATG GAA GAG GCG AGC CAG     192
Thr Arg Asp Leu Glu Lys His Cys Arg Asp Met Glu Glu Ala Ser Gln
        50                  55                  60

CGC AAG TGG AAT TTC GAT TTT CAG AAT CAC AAA CCC CTA GAG GGC AAG     240
Arg Lys Trp Asn Phe Asp Phe Gln Asn His Lys Pro Leu Glu Gly Lys
65                  70                  75

TAC GAG TGG CAA GAG GTG GAG AAG GGC AGC TTG CCC GAG TTC TAC TAC     288
Tyr Glu Trp Gln Glu Val Glu Lys Gly Ser Leu Pro Glu Phe Tyr Tyr
    80                  85                  90                  95

AGA CCC CCG CGG CCC CCC AAA GGT GCC TGC AAG GTG CCG GCG CAG GAG     336
Arg Pro Pro Arg Pro Pro Lys Gly Ala Cys Lys Val Pro Ala Gln Glu
                100                 105                 110

AGC CAG GAT GTC AGC GGG AGC CGC CCG GCG GCG CCT TTA ATT GGG GCT     384
Ser Gln Asp Val Ser Gly Ser Arg Pro Ala Ala Pro Leu Ile Gly Ala
            115                 120                 125

CCG GCT AAC TCT GAG GAC ACG CAT TTG GTG GAC CCA AAG ACT GAT CCG     432
Pro Ala Asn Ser Glu Asp Thr His Leu Val Asp Pro Lys Thr Asp Pro
        130                 135                 140

TCG GAC AGC CAG ACG GGG TTA GCG GAG CAA TGC GCA GGA ATA AGG AAG     480
Ser Asp Ser Gln Thr Gly Leu Ala Glu Gln Cys Ala Gly Ile Arg Lys
145                 150                 155

CGA CCT GCA ACC GAC GAT TCT TCT ACT CAA AAC AAA AGA GCC AAC AGA     528
Arg Pro Ala Thr Asp Asp Ser Ser Thr Gln Asn Lys Arg Ala Asn Arg
160                 165                 170                 175

ACA GAA GAA AAT GTT TCA GAC GGT TCC CCA AAT GCC GGT TCT GTG GAG     576
Thr Glu Glu Asn Val Ser Asp Gly Ser Pro Asn Ala Gly Ser Val Glu
                180                 185                 190

CAG ACG CCC AAG AAG CCT GGC CTC AGA AGA CGT CAA ACG GGT GGC GGG     624
Gln Thr Pro Lys Lys Pro Gly Leu Arg Arg Arg Gln Thr Gly Gly Gly
            195                 200                 205

GGC AGC GGG GGT GGC GGT TCC GGC GGG GGT GGA TCC GAA TTC TGC GGC     672
Gly Ser Gly Gly Gly Gly Ser Gly Gly Gly Gly Ser Glu Phe Cys Gly
        210                 215                 220

CGC GCG TGC GCT CGG CGG CTG CGG AGA GGG GAG AGC ATG CAG CGG GCG     720
Arg Ala Cys Ala Arg Arg Leu Arg Arg Gly Glu Ser Met Gln Arg Ala
225                 230                 235

GCG GGG AGC AGC ATG GAG CCT TCG GCT GAC TGG CTG GCC ACG GCC GCG     768
Ala Gly Ser Ser Met Glu Pro Ser Ala Asp Trp Leu Ala Thr Ala Ala
240                 245                 250                 255

GCC CGG GGT CGG GTA GAG GAG GTG CGG GCG CTG CTG GAG GCG GTG GCG     816
Ala Arg Gly Arg Val Glu Glu Val Arg Ala Leu Leu Glu Ala Val Ala
                260                 265                 270
```

```
CTG  CCC  AAC  GCA  CCG  AAT  AGT  TAC  GGT  CGG  AGG  CCG  ATC  CAG  GTC  ATG        864
Leu  Pro  Asn  Ala  Pro  Asn  Ser  Tyr  Gly  Arg  Arg  Pro  Ile  Gln  Val  Met
          275                      280                          285

ATG  ATG  GGC  AGC  GCC  CGA  GTG  GCG  GAG  CTG  CTG  CTG  CTC  CAC  GGC  GCG        912
Met  Met  Gly  Ser  Ala  Arg  Val  Ala  Glu  Leu  Leu  Leu  Leu  His  Gly  Ala
          290                      295                          300

GAG  CCC  AAC  TGC  GCC  GAC  CCC  GCC  ACT  CTC  ACC  CGA  CCC  GTG  CAC  GAC        960
Glu  Pro  Asn  Cys  Ala  Asp  Pro  Ala  Thr  Leu  Thr  Arg  Pro  Val  His  Asp
          305                      310                          315

GCT  GCC  CGG  GAG  GGC  TTC  CTG  GAC  ACG  CTG  GTG  GTG  CTG  CAC  CGG  GCC       1008
Ala  Ala  Arg  Glu  Gly  Phe  Leu  Asp  Thr  Leu  Val  Val  Leu  His  Arg  Ala
320                      325                      330                          335

GGG  GCG  CGG  CTG  GAC  GTG  CGC  GAT  GCC  TGG  GGC  CGT  CTG  CCC  GTG  GAC       1056
Gly  Ala  Arg  Leu  Asp  Val  Arg  Asp  Ala  Trp  Gly  Arg  Leu  Pro  Val  Asp
                         340                      345                     350

CTG  GCT  GAG  GAG  CTG  GGC  CAT  CGC  GAT  GTC  GCA  CGG  TAC  CTG  CGC  GCG       1104
Leu  Ala  Glu  Glu  Leu  Gly  His  Arg  Asp  Val  Ala  Arg  Tyr  Leu  Arg  Ala
                    355                      360                     365

GCT  GCG  GGG  GGC  ACC  AGA  GGC  AGT  AAC  CAT  GCC  CGC  ATA  GAT  GCC  GCG       1152
Ala  Ala  Gly  Gly  Thr  Arg  Gly  Ser  Asn  His  Ala  Arg  Ile  Asp  Ala  Ala
               370                      375                     380

GAA  GGT  CCC  TCA  GAC  ATC  CCC  GAT  TGAAAGAACC  AGAGAGGCTC  TGAGAAACCT            1206
Glu  Gly  Pro  Ser  Asp  Ile  Pro  Asp
          385                      390

CGGGAAACTT  AGATCATCAG  TCACCGAAGG  TCCTACAGGG  CCACAACTGC  CCCCGCCACA                1266

ACCCACCCCG  CTTTCGTAGT  TTTCATTTAG  AAAATAGAGC  TTTTAAAAAT  GTCCTGCCTT                1326

TTAACGTAGA  TATAAGCCTT  CCCCCACTAC  CGTAAATGTC  CATTTATATC  ATTTTTTATA                1386

TATTCTTATA  AAAATGTAAA  AAAGAAAACT  CGAG                                              1420
```

(2) INFORMATION FOR SEQ ID NO:2:

(i) SEQUENCE CHARACTERISTICS:
        (A) LENGTH: 391 amino acids
        (B) TYPE: amino acid
        (D) TOPOLOGY: linear (ii) MOLECULE TYPE: protein (xi) SEQUENCE DESCRIPTION: SEQ ID NO:2:

```
Met  His  His  His  His  His  His  Ser  Asn  Val  Arg  Val  Ser  Asn  Gly  Ser
 1                    5                     10                         15

Pro  Ser  Leu  Glu  Arg  Met  Asp  Ala  Arg  Gln  Ala  Glu  His  Pro  Lys  Pro
               20                    25                         30

Ser  Ala  Cys  Arg  Asn  Leu  Phe  Gly  Pro  Val  Asp  His  Glu  Glu  Leu  Thr
          35                         40                         45

Arg  Asp  Leu  Glu  Lys  His  Cys  Arg  Asp  Met  Glu  Glu  Ala  Ser  Gln  Arg
     50                         55                    60

Lys  Trp  Asn  Phe  Asp  Phe  Gln  Asn  His  Lys  Pro  Leu  Glu  Gly  Lys  Tyr
 65                    70                    75                          80

Glu  Trp  Gln  Glu  Val  Glu  Lys  Gly  Ser  Leu  Pro  Glu  Phe  Tyr  Tyr  Arg
                    85                    90                          95

Pro  Pro  Arg  Pro  Pro  Lys  Gly  Ala  Cys  Lys  Val  Pro  Ala  Gln  Glu  Ser
              100                       105                      110

Gln  Asp  Val  Ser  Gly  Ser  Arg  Pro  Ala  Ala  Pro  Leu  Ile  Gly  Ala  Pro
              115                       120                      125

Ala  Asn  Ser  Glu  Asp  Thr  His  Leu  Val  Asp  Pro  Lys  Thr  Asp  Pro  Ser
130                       135                      140
```

```
Asp  Ser  Gln  Thr  Gly  Leu  Ala  Glu  Gln  Cys  Ala  Gly  Ile  Arg  Lys  Arg
145                 150                 155                 160

Pro  Ala  Thr  Asp  Asp  Ser  Ser  Thr  Gln  Asn  Lys  Arg  Ala  Asn  Arg  Thr
               165                 170                 175

Glu  Glu  Asn  Val  Ser  Asp  Gly  Ser  Pro  Asn  Ala  Gly  Ser  Val  Glu  Gln
          180                      185                      190

Thr  Pro  Lys  Lys  Pro  Gly  Leu  Arg  Arg  Gln  Thr  Gly  Gly  Gly  Gly
          195                 200                 205

Ser  Gly  Gly  Gly  Gly  Ser  Gly  Gly  Gly  Gly  Ser  Glu  Phe  Cys  Gly  Arg
     210                 215                      220

Ala  Cys  Ala  Arg  Arg  Leu  Arg  Arg  Gly  Glu  Ser  Met  Gln  Arg  Ala  Ala
225                      230                 235                           240

Gly  Ser  Ser  Met  Glu  Pro  Ser  Ala  Asp  Trp  Leu  Ala  Thr  Ala  Ala  Ala
               245                      250                      255

Arg  Gly  Arg  Val  Glu  Glu  Val  Arg  Ala  Leu  Leu  Glu  Ala  Val  Ala  Leu
               260                 265                      270

Pro  Asn  Ala  Pro  Asn  Ser  Tyr  Gly  Arg  Arg  Pro  Ile  Gln  Val  Met  Met
          275                      280                 285

Met  Gly  Ser  Ala  Arg  Val  Ala  Glu  Leu  Leu  Leu  Leu  His  Gly  Ala  Glu
     290                      295                 300

Pro  Asn  Cys  Ala  Asp  Pro  Ala  Thr  Leu  Thr  Arg  Pro  Val  His  Asp  Ala
305                      310                 315                           320

Ala  Arg  Glu  Gly  Phe  Leu  Asp  Thr  Leu  Val  Val  Leu  His  Arg  Ala  Gly
                    325                      330                      335

Ala  Arg  Leu  Asp  Val  Arg  Asp  Ala  Trp  Gly  Arg  Leu  Pro  Val  Asp  Leu
               340                      345                 350

Ala  Glu  Glu  Leu  Gly  His  Arg  Asp  Val  Ala  Arg  Tyr  Leu  Arg  Ala  Ala
          355                      360                 365

Ala  Gly  Gly  Thr  Arg  Gly  Ser  Asn  His  Ala  Arg  Ile  Asp  Ala  Ala  Glu
     370                 375                      380

Gly  Pro  Ser  Asp  Ile  Pro  Asp
385                 390
```

( 2 ) INFORMATION FOR SEQ ID NO:3:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GCGGCCGGTC ATATGCACCA CCATCACCAT CACTCAAACG TGCGAGTGTC T          51
```

( 2 ) INFORMATION FOR SEQ ID NO:4:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
GCCGCCGGCG TCGACTCGGC CGAATTCGGA TCCACCCCCG CCGGAACCGC CACCCCCGCT          60
GCCCCCGCCA CCCGTTTGAC GTCTTCTGAG GCCAGG                                   96
```